United States Patent
Katragadda et al.

(10) Patent No.: US 7,521,917 B2
(45) Date of Patent: Apr. 21, 2009

(54) METHOD AND APPARATUS FOR TESTING MATERIAL INTEGRITY

(75) Inventors: Gopichand Katragadda, Karnataka (IN); Manoj Kumar Koyithitta Meethal, Kerala (IN); Slvaramanivas Ramaswamy, Karnataka (IN); Amitabha Dutta, Orissa (IN)

(73) Assignee: General Electric Company, Niskayuna, NY (US)

( * ) Notice: Subject to any disclaimer, the term of this patent is extended or adjusted under 35 U.S.C. 154(b) by 307 days.

(21) Appl. No.: 10/876,928

(22) Filed: Jun. 25, 2004

(65) Prior Publication Data
US 2005/0285588 A1 Dec. 29, 2005

(51) Int. Cl.
*G01R 33/00* (2006.01)
(52) U.S. Cl. .................. 324/126; 324/228; 324/238
(58) Field of Classification Search .............. None
See application file for complete search history.

(56) References Cited

U.S. PATENT DOCUMENTS

| | | | | |
|---|---|---|---|---|
| 1,958,079 A * | 5/1934 | Billstein | ............ | 324/217 |
| 2,049,764 A * | 8/1936 | Drake | ............ | 324/260 |
| 2,106,694 A * | 1/1938 | Grindall et al. | ............ | 324/218 |
| 2,884,592 A * | 4/1959 | Wilson | ............ | 324/217 |
| 6,424,150 B2 * | 7/2002 | Kwun et al. | ............ | 324/216 |
| 6,696,982 B2 * | 2/2004 | Yoshioka et al. | ............ | 340/988 |
| 6,768,298 B2 * | 7/2004 | Katragadda et al. | ............ | 324/217 |
| 2002/0065610 A1 * | 5/2002 | Clark et al. | ............ | 702/35 |

OTHER PUBLICATIONS

W. Lord, et al.; "A Finite Element Study of Remote Field Eddy Current Phenomenon", IEEE Transactions on Magnetics, vol. 24, Jan. 1998, pp. 435-438.

* cited by examiner

*Primary Examiner*—Minh N Tang
(74) *Attorney, Agent, or Firm*—Patrick K. Patnode

(57) ABSTRACT

In accordance with one embodiment, the present technique provides a testing apparatus for testing material integrity in an object. The testing apparatus includes an electrical conductor and a sensing device. In the exemplary testing device, the electrical conductor extends in a generally linear direction and is configured to route current in a direction generally transverse to a longitudinal axis of the object being tested. Routing of current through the electrical conductor creates remote field eddy current effect, which, in turn, affects a magnetic field around the test object. The testing apparatus also includes a sensing device located at a distance from the electrical conductor and configured to detect magnetic fields generated in response to current routed through the electrical conductor.

34 Claims, 4 Drawing Sheets

METHOD AND APPARATUS FOR TESTING MATERIAL INTEGRITY

BACKGROUND

The present invention relates generally to a technique for inspecting materials and testing material integrity. Particularly, the present invention relates to methods and apparatus for testing material integrity via remote field eddy current techniques.

Detecting presence of defects, such as cracks, in materials can assist maintenance technicians in predicting and mitigating likelihood of malfunction in these materials. By way of example, rails and/or railheads in railroad transportation systems can have horizontal defects, transverse defects, and combinations thereof. Generally, horizontal defects in a rail are parallel to a longitudinal axis of the rail. For example, shelling and horizontal split-heads are types of horizontal defects that are commonly found in rails and railheads. Generally, shelling occurs on a surface of the rail when a cold worked layer separates from a bottom layer and flows over the bottom layer. Transverse defects, however, are generally perpendicular to the longitudinal axis of the rail. Under certain conditions, these transverse defects can propagate under the fatigue of cyclic use. Over time, the horizontal and transverse defects (e.g., cracks) can lead to malfunction of the rail and/or railhead, leading to undesirable maintenance costs and downtimes, for instance.

Traditionally, rails and railheads are inspected using both visual and non-visual (i.e., non-destructive) techniques. By way of example, non-destructive testing techniques include ultrasonic techniques (e.g., with forward-looking ultrasonic transducers, side-looking ultrasonic transducers, etc.), electromagnetic techniques such as induction coiled-conductor techniques and magnetic induction techniques to name but a few.

However, these traditional techniques are not without their problems. For example, during ultrasonic testing techniques, horizontal defects can mask transverse defects and, as such, prevent detection of these underlying transverse defects. That is, the horizontal defects (e.g., shelling) can reflect ultrasonic signals, thereby masking the transverse defects located underneath the horizontal defects (e.g. detail fracture in rails). Furthermore, ultrasonic techniques generally limit a speed at which the testing can be conducted.

Furthermore, coiled-conductor induction techniques, which use low frequency power to induce currents in the testing material, are negatively affected by skin effect, which can limit an effective inspection depth of inspection system. Moreover, coiled-conductor induction techniques are also limited by the speed at which the testing can be conducted.

Thus, there exists a need for improved inspection system for detecting defects in the materials to determine the integrity of the material.

BRIEF DESCRIPTION

In accordance with one embodiment, the present technique provides a testing apparatus for testing integrity of an object. The exemplary testing apparatus has an electrical conductor that extends in a generally linear direction and that is configured to route current in a direction generally transverse to a longitudinal axis of the object being tested. The testing apparatus also includes a sensing device located at a distance from the electrical conductor and configured to detect magnetic fields generated in response to current routed through the electrical conductor.

In accordance with another embodiment, the present technique provides a method of testing integrity of an object. The exemplary method includes routing an electric current through an electrical conductor in a direction generally transverse to a longitudinal axis of the object being tested. The routing current induces eddy current through the electrical conductor in the object that, in turn, produces magnetic fields. The method further includes sensing the magnetic fields generated at a distance from the electrical conductor.

DRAWINGS

These and other features, aspects, and advantages of the present invention will become better understood when the following detailed description is read with reference to the accompanying drawings in which like characters represent like parts throughout the drawings, wherein.

Figure 5:
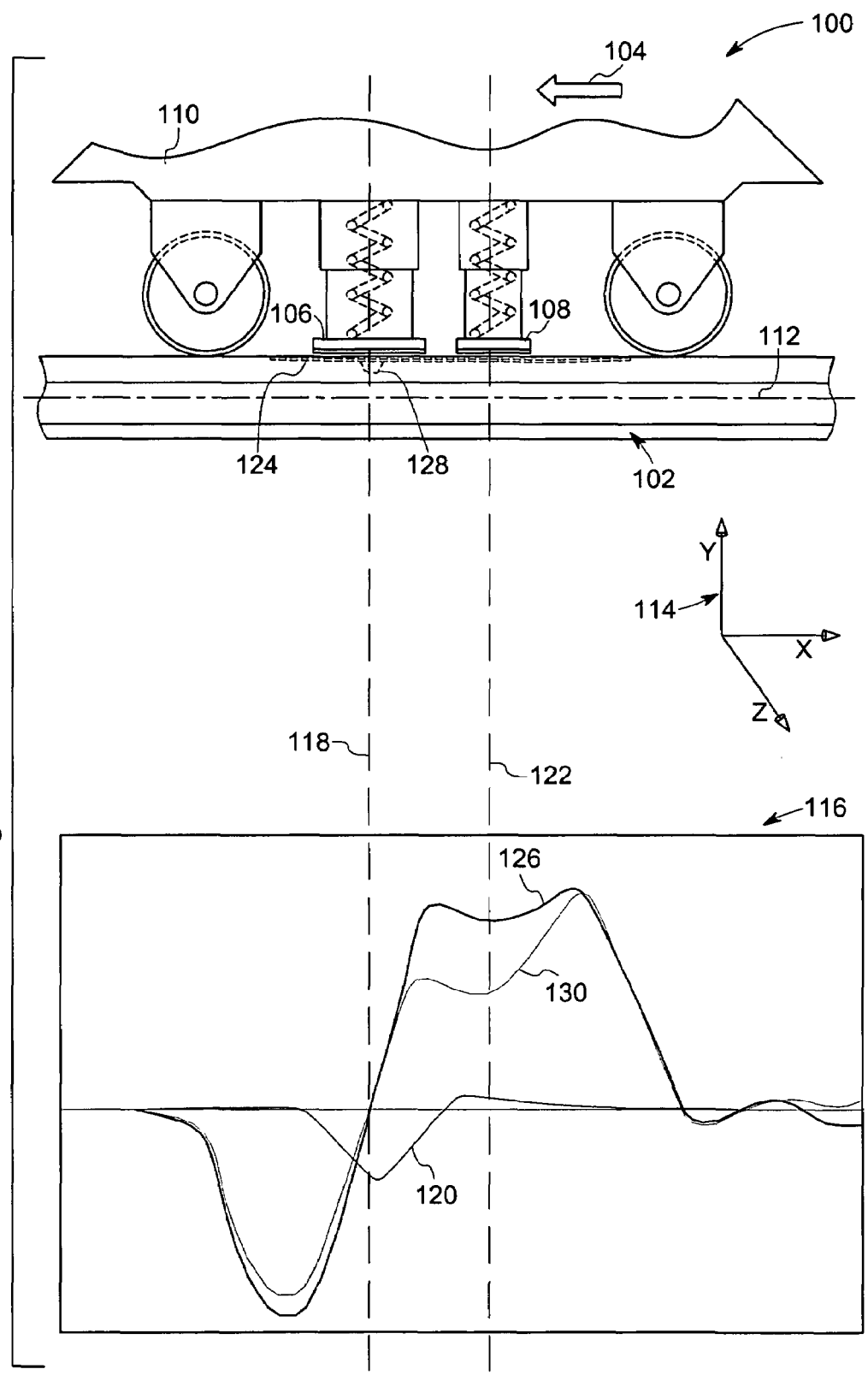
Figure 6:
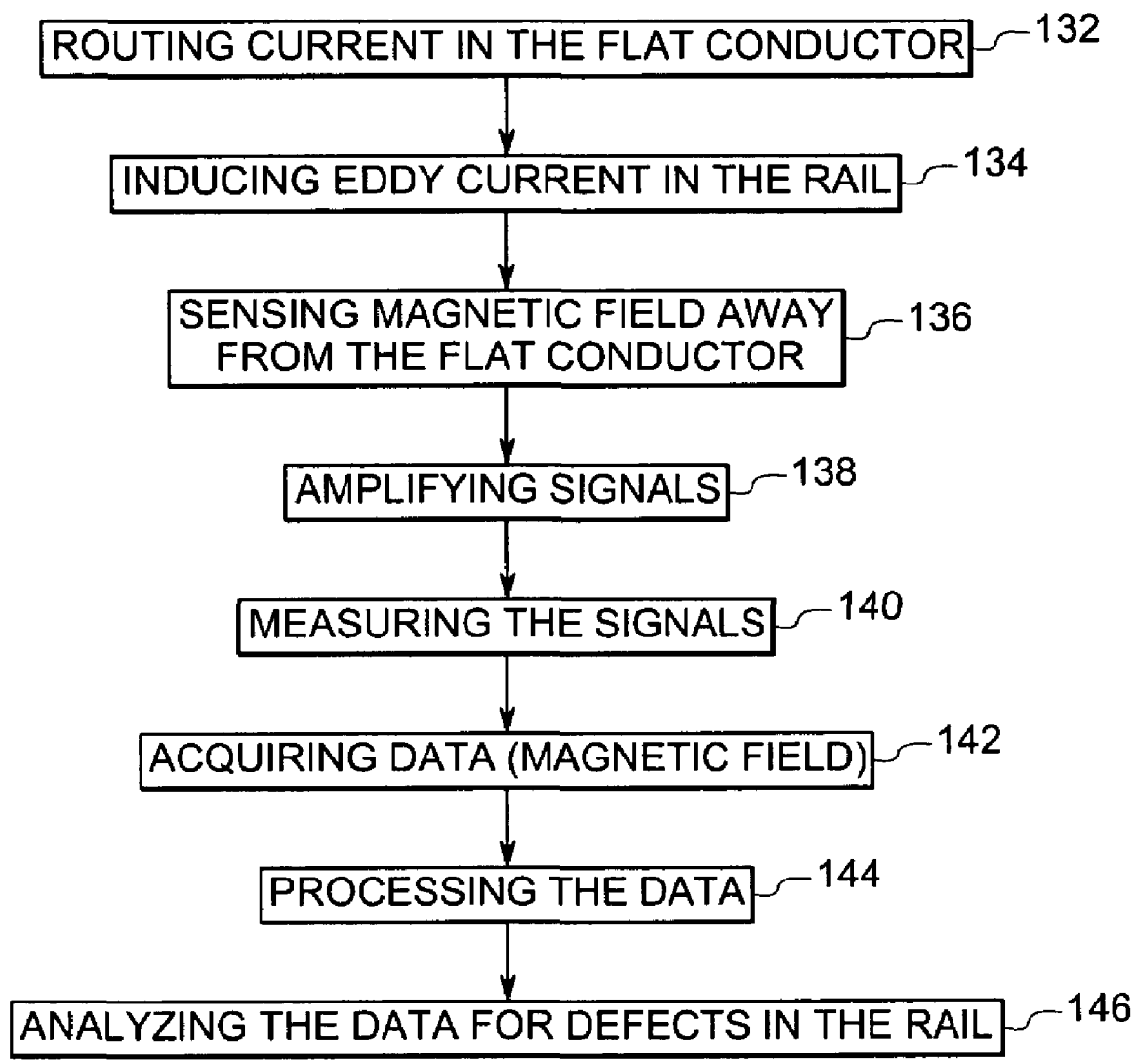

FIG. 5 graphically represents a measured magnetic field component during operation of an exemplary testing carriage, in accordance with an embodiment of the present technique; and FIG. 6 is a flowchart illustrating an exemplary process for detecting defects in rails, in accordance with an embodiment of present technique.

DETAILED DESCRIPTION

The present technique is directed towards testing integrity of an object and for detecting defects in the object. Although following discussion focuses on testing apparatus and methods for rails, those skilled in the art will recognize in light of the following discussion that the present technique is applicable to a wide variety of testing environments and settings. For example, the present technique may be applicable to testing of plates, bars and support structures, to name but a few applications.

Figure 1:
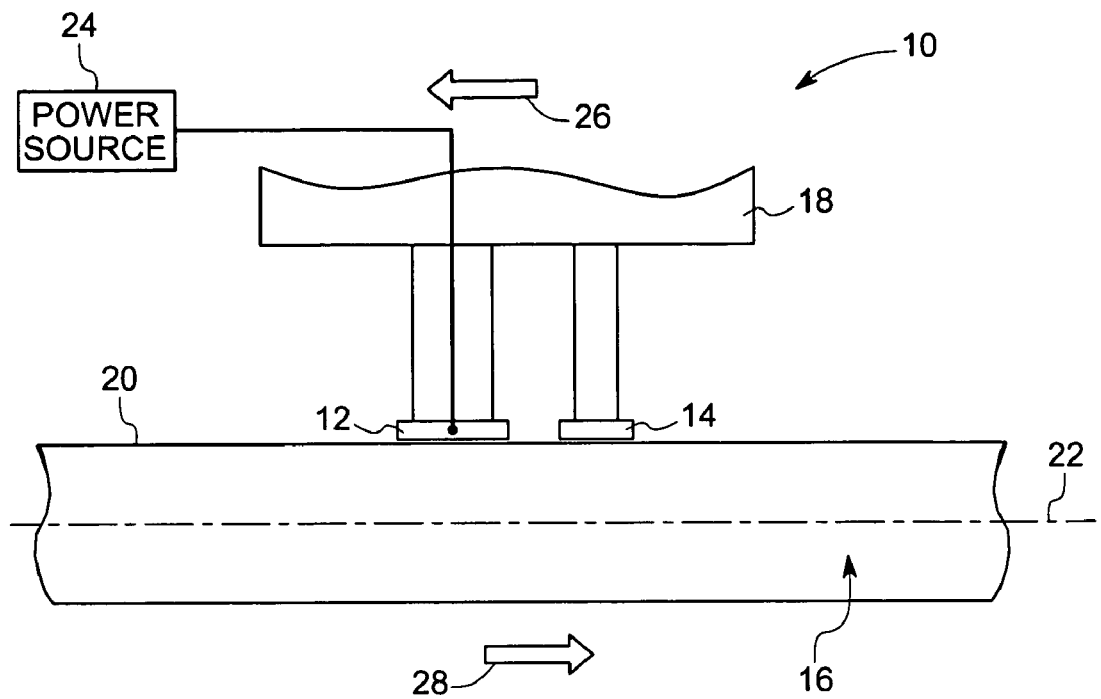
FIG. 1 is a diagrammatic representation of a testing apparatus for testing integrity of an object, in accordance with an embodiment of present technique.

Turning now to the drawings, FIG. 1 illustrates an exemplary testing apparatus 10 for testing the integrity of an object, which is made of ferromagnetic material. As depicted, the exemplary testing apparatus 10 has an electrical conductor 12 and a magnetic-field sensor 14 that, along with other components, cooperate to test the integrity of an object 16 and to detect defects in the object 16. In the exemplary embodiment, the electrical conductor 12 and the magnetic-field sensor 14 are mounted to a testing apparatus body, such as an exemplary carrier structure 18. To induce current within the test object 16, and to detect changes in the magnetic field due to current routed through the electrical conductor 12, the electrical conductor 12 and the magnetic-field sensor 14 in the exemplary testing apparatus 10 are located relatively close to the object 16. Additionally, the electrical conductor 12 and the magnetic-field sensor 14 are located outboard of an external surface 20 of the test object 16.

In the exemplary testing apparatus 10, the electrical conductor 12 is a flat electrical conductor that extends in a generally linear direction and that is configured to route current a direction generally transverse to a longitudinal axis 22 of the test object 16. Current, in the exemplary apparatus 10, is provided by a power source 24. As discussed further below, the power source 24 may provide direct current (dc) power and/or alternating current (ac) power to the electrical conductor 12. By routing current through the electrical conductor (i.e., exciting the electrical conductor), certain electromagnetic effects occur. For example, current routed through the electrical conductor creates a magnetic field and induces eddy currents within the test object. These eddy currents, in turn, generate their own magnetic fields that are detected by the magnetic-field sensor 14, for instance. By way of example, the magnetic-field sensor 14 may be a bank of Hall effect sensors, a giant magneto-resistive (GMR) sensors, or any other suitable type of magnetic-field sensor. In the exemplary testing apparatus 10, the magnetic-field sensor 14 is configured to detect magnetic fields generated at a distance behind the electrical conductor 12. In the illustrated testing apparatus 10, the magnetic-field sensor 14 is located behind the electrical conductor 12. As discussed further below, defects in the test object, such as transverse cracks, affect the magnetic fields generated in response to current routed through the electrical conductor 12. By sensing and analyzing these magnetic fields, defects in the test object 16 can be detected.

To test for defects in the object 16, the testing apparatus 10 and the test object 16 can be positioned with respect to one another, thereby facilitating the creation of what is known in the pertinent art as a remote field eddy current (RFEC) effect. In one exemplary embodiment, the object 16 remains stationary, while the testing apparatus 10 moves relative to the object 16, as represented by directional arrow 26. In another exemplary embodiment, the testing apparatus 10 remains stationary, while the object 16 moves relative to the testing apparatus 10, as represented by directional arrow 28. As will be appreciated by those of ordinary skill in the art, the directions 26 and 28 are merely exemplary directions, and other directions of relative motion can be envisaged. By way of example, both the test object 16 and the testing apparatus 10 can be in motion with respect to one another. In situations where there is a relative motion between the testing apparatus 10 and the object 16, the power source 24 may provide dc power or ac power to the electrical conductor 12. By way of example, ac power may be of any suitable frequency, including frequencies between 100 to 300 Hz.

In yet another embodiment, both the testing apparatus 10 and the object 16 remain stationary with respect to one another. That is, there is no relative motion between the two structures. In this exemplary embodiment, where there is no relative motion between the test object 16 and the testing apparatus 10, the power source 24 provides ac power to the electrical conductor 12. As discussed above, ac power may be of any number of suitable frequencies, such as frequencies between 100 and 300 Hz, for instance. By routing ac current through the electrical conductor, an RFEC effect can be created in the test object 16, even when both the test object 16 and the testing apparatus 10 remain stationary with respect to one another.

Figure 2:
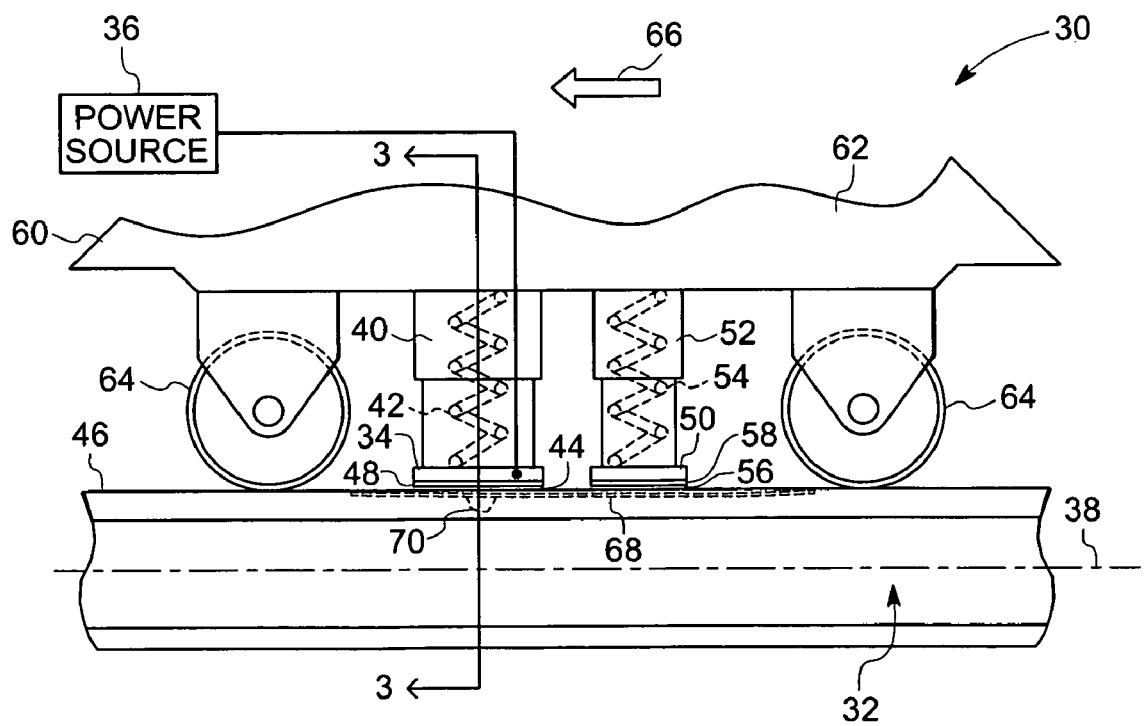
FIG. 2 is a diagrammatic representation of a testing carriage on a railroad rail, in accordance with an embodiment of present technique.

FIG. 2 is a diagrammatic illustration of an exemplary embodiment of a rail testing apparatus 30 for testing material integrity of a rail 32. As illustrated, an exemplary rail testing apparatus 30 includes an electrical conductor 34, which is coupled to a power source 36. The exemplary electrical conductor 34 is a substantially flat electrical conductor that extends in a linear direction and that is generally perpendicular to a longitudinal axis 38 of the rail 32. Accordingly, the electrical conductor 34 is configured to route current in a direction generally transverse to the longitudinal axis 38 of the rail 32, thereby limiting directions in which certain electromagnetic effects occur. Advantageously, the exemplary electrical conductor 34 is mounted to a telescopic support structure 40 that facilitates adjustment of a height at which the electrical conductor is located. By way of example, the exemplary support structure 40 includes a compression spring 42 that biases the electrical conductor 34 towards the rail 32. By biasing the electrical conductor 34, a narrow gap 44, which is be less than 1 mm in the exemplary embodiment, is maintained between the electrical conductor 34 and an external surface 46 of the rail 32. Advantageously, to mitigate a likelihood of damage to the electrical conductor 34, the exemplary testing apparatus 30 includes an anti-friction pad 48 that is secured to the electrical conductor 34 and is located between the electrical conductor 34 and the external surface 46 of the rail 32.

The exemplary rail testing apparatus 30 also includes a magnetic-field sensor 50. In certain embodiments, the magnetic-field sensor 50 includes a Hall effect sensor, a giant magneto-resistive (GMR) sensor, or any other suitable type of magnetic-field sensor. Indeed, in certain embodiments, the testing apparatus includes a bank of magnetic-field sensors 50 that are of various types. Similar to the electrical conductor 34, the magnetic-field sensor 50 of the exemplary rail testing apparatus is mounted to a telescopic support structure 52, which includes a compression spring 54 that biases the magnetic-field sensor 50 towards the external surface 46 of the rail 32. As explained above, the spring 54 and support 52 cooperate to provide a narrow gap 56 between the magnetic-field sensor 50 and the external surface 46 of the rail 32. Again, this gap 56, in certain embodiments, is less than 1 mm, for example. To reduce a likelihood of wear, the exemplary magnetic-field sensor 50 includes an anti-friction pad 58 that is secured to the magnetic-field sensor 50 and that is located between the magnetic-field sensor 50 and the external surface 46 of the rail 32.

In the exemplary embodiment, the rail testing apparatus 30 includes a carrier structure 60 to which the flat electrical conductor 34 and the magnetic-field sensor 50 are mounted. The exemplary carrier structure 60 includes a body 62 and wheels 64, which configured to roll over and engage with the rail 32. The testing apparatus 30 is configured to move over the rail 32 in a testing direction, as indicated generally by directional arrow 66. This testing direction 66 is generally parallel with the rail's longitudinal axis 38. By way of example, the exemplary rail testing apparatus 30 is configured to travel along the rail at various speeds. Indeed, the exemplary testing apparatus 30, in certain embodiment, is configured to travel along the rail at a speed as low as 10 kilometers per hour to as high as 110 kilometers per hour, and beyond, to test the material integrity of the rail 32. The exemplary magnetic-field sensor 50 is mounted adjacent to the flat electrical conductor 34 in a direction opposite to the direction of the motion 66 of the carrier structure 60.

As depicted in FIG. 2, reference numeral 68 generally denotes a horizontal defect or shelling in the rail 32 that is generally parallel to the longitudinal axis 38 of the rail 32. Reference numeral 70 indicates a transverse defect, which is generally perpendicular to the longitudinal axis of the rail 32.

As the carrier structure 60 travels in the testing direction 66, it carries the flat electrical conductor 34 and the magnetic-field sensor 50 in the testing direction 66 as well. An electric current, which is provided by the power source 36, is routed through the flat electrical conductor 34 in cooperation with other components, for testing the material integrity of the rail 32. Again, the power source may provide ac power and/or dc power to the flat electrical conductor 34. Electric current that is routed through the flat electrical conductor 34 induces eddy currents in the rail 32, which, in turn, generate their own magnetic fields. These magnetic fields, however, are affected by properties of the rail. That is, these resultant magnetic fields are affected by defects in the rail 32. Thus, as discussed further below, the magnetic fields will be different for a section without any defect, a section with horizontal defects (shelling), and a section with transverse defects under the shelling. Hence, as discussed further below, interpretation of data from the magnetic-field sensor 50 can be used to identify defects in the rail 32.

Figure 3:
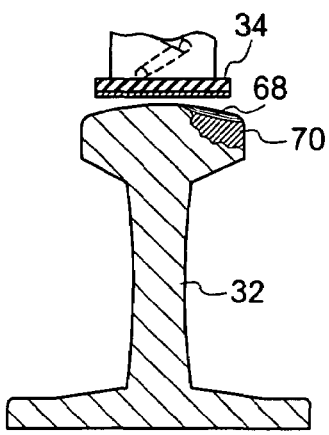
FIG. 3 is a partial and diagrammatic cross-sectional view of the rail and testing carriage of FIG. 2 along line 3-3, illustrating exemplary defects within the rail.

FIG. 3 is a partial cross-sectional view of the rail 32 along line 3-3 of FIG. 2. As can be seen in FIG. 3, the horizontal defect or shelling 68, can occur above transverse defects 70.

Figure 4:
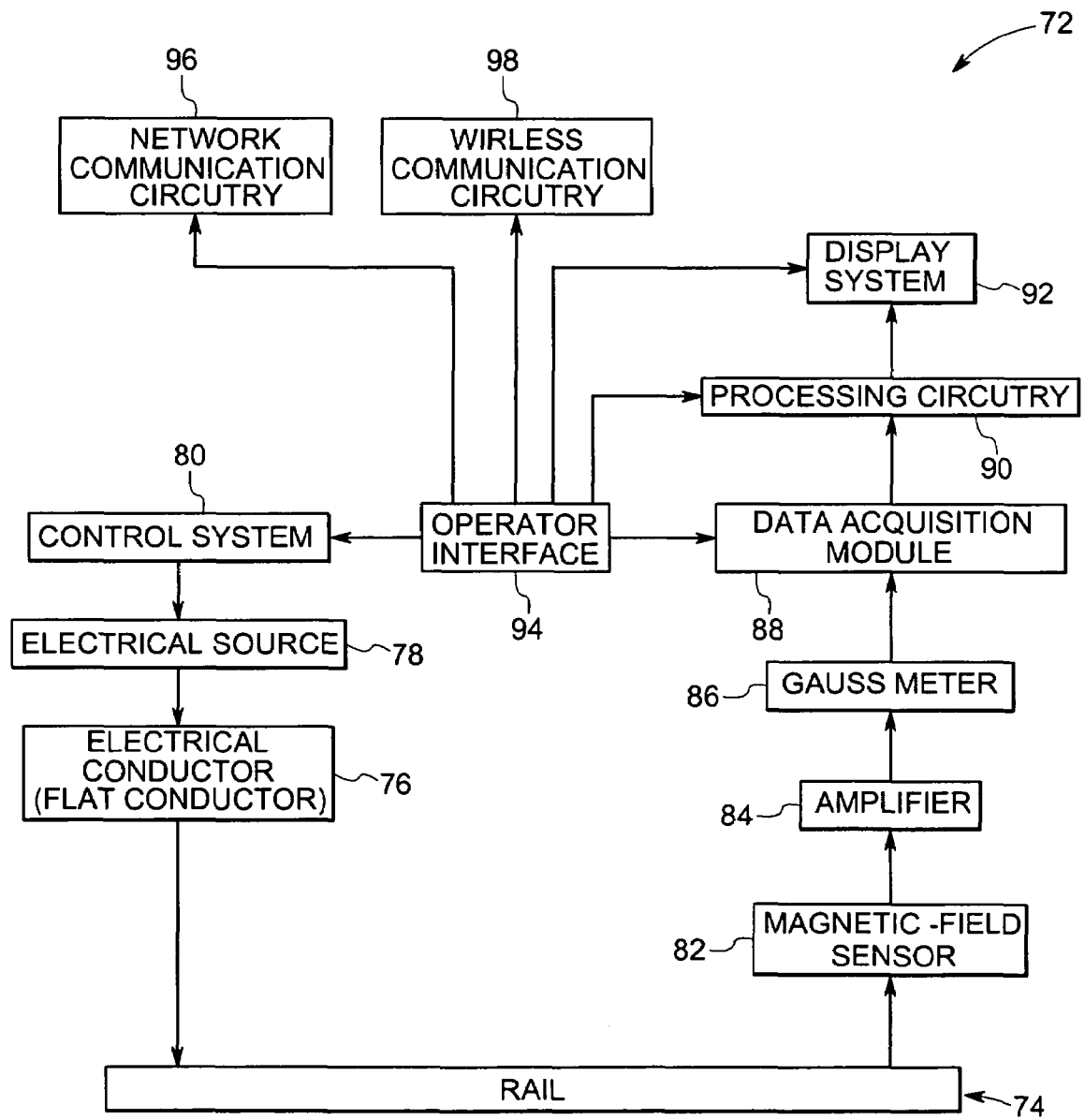
FIG. 4 is a diagrammatic representation of various components of a testing apparatus for testing rails, in accordance with an embodiment of present technique.

FIG. 4 is a diagrammatic illustration of various components of a rail testing apparatus 72 for detecting defects in a rail 74. The exemplary rail testing apparatus 72 includes a flat electrical conductor 76 that is mounted relatively close to the rail 74. The flat electrical conductor 76 is coupled to a power source 78, which, in certain embodiments, provides ac and/or dc power. In certain embodiments, the power source 78 comprises a pulse width modulated power source. In the exemplary testing apparatus 72, the power source 78 is under the direction of a control system 80.

The testing apparatus 72 also includes a magnetic-field sensor 82. Again, the magnetic-field sensor 82 may be a Hall effect sensor, a giant magneto-resistive (GMR) sensor, or another other type of suitable magnetic-field sensor. The magnetic-field sensor 82 may be part of an array of magnetic-field sensors, which can include different types of sensors. The exemplary magnetic-field sensor 82 produces signals in response to sensed magnetic fields. These signals from the magnetic-field sensor 82 are indicative of characteristics of the sensed magnetic fields. The magnetic-field sensor 82 is coupled to an amplifier 84, which is in communication with the magnetic-field sensor and amplifies the signals from the magnetic-field sensor 82. In turn, the exemplary amplifier 84 is coupled to a gauss-meter 86, which measures (i.e., quantifies) the amplified signals from the amplifier 84. The gauss-meter 86, in certain embodiments, couples to a data acquisition module 88, which gathers magnetic field data from the gauss-meter 86. Processing circuitry 90, which, in certain embodiments includes various types of logic devices, such as a programmable logic circuit (PLC), a processor, to name a few types of logic circuits, processes data from the data acquisition module 88. As discussed further below, the exemplary processing circuitry 90 interprets the data from the data acquisition module by correlating the data to known magnetic field patterns for certain defects. The exemplary testing apparatus 72 also includes a display system 92, which is configured to display information from the processing circuitry 90. By way of example, the display system comprises a light emitting diode (LED), a liquid crystal display (LCD), to name but a few types of displays.

In the exemplary embodiment, an operator controls the testing apparatus 72 via an operator interface 94, such as a keyboard, a mouse, and other suitable user interaction devices. The exemplary operator interface 94 is coupled to the control system 80, the data acquisition module 88, the processing circuitry 90 and the display system 92. The exemplary testing apparatus 72 is connected to a network via network communication circuitry 96, which facilitates communications with a network in accordance with a network communication protocol. The testing apparatus may further be connected to a wireless communication circuitry 98, thereby facilitating wireless communications with remote systems and devices. Advantageously, the exemplary network communication circuitry and the wireless communication circuitry can facilitate remote control, operations, and communications with respect to the exemplary testing apparatus 72.

FIG. 5 illustrates exemplary behavior of magnetic fields for different conditions of a rail in relation to positions of an electrical conductor and a magnetic-field sensor in accordance with aspects of present technique. As depicted, a testing exemplary rail testing apparatus 100 moves over a rail 102 in a testing direction, as represented by directional arrow 104. Similar to rail testing apparatus 72, testing apparatus 100 has a flat electrical conductor 106, a magnetic-field sensor 108, and a carrier structure 110. In the exemplary embodiment, the electrical conductor 106 is a substantially flat electrical conductor that extends in a generally linear direction with respect to a longitudinal axis 112 of the rail 102. Moreover, the exemplary electrical conductor 106 routes current in a direction generally transverse to the longitudinal axis 112 of the rail 102.

As discussed above, routing electrical current through the electrical conductor 106 causes certain electromagnetic effects. As one example, routing current through the electrical conductor 106 and, in certain case, movement of the testing apparatus 100 creates RFEC effect in the rail 102.

With respect to the orientation of the FIG. 5, a rectangular coordinate system 114 is illustrated. In this coordinate system 114, the positive X-axis extends to the right of the page, the positive Y-axis extends to the top of the page, and the positive Z-axis extends out of the page. With this in mind, the exemplary conductor 106 routes current in the Z-axis direction and, as such, across the rail 102.

Keeping the rectangular coordinate system 114 in mind, graph 116 illustrates the behavior of exemplary magnetic fields, which are sensed and detected by the magnetic-field sensor 108. Specifically, the graph 116 illustrates magnetic field components (i.e., magnetic flux density) in the direction of the Z-axis plotted versus the location in the rail 102.

In the graph 116, dashed line 118 represents a location of the midpoint of the electrical conductor 106. Because of current routed in the electrical conductor and/in certain instances, movement of the rail testing apparatus 100, RFEC effect is created in the rail 102 behind the electrical conductor (i.e., to the right of dashed line 118). These RFEC effect, in turn, affects the magnetic field in the region behind the electrical conductor at an exemplary location as represented by the dashed line 122. Curve 120 represents the magnetic flux density in the Z-axis direction when the rail 102 has no defect. As can be seen, the magnetic flux density in the Z-axis direction approaches zero relatively close to an excitation point of the electrical conductor 106. However, presence of defects in the rails affects the detected magnetic flux density. For example, the presence of a horizontal defect, such as the illustrated shelling 124, increases the magnetic field density produced in the Z-axis direction in response to current routing through the electrical conductor 106. In the graph 116, curve 126 represents the magnetic flux density of a rail having shelling 124. As illustrated, the shelling 124 causes the magnetic field density in the Z-axis direction to increase behind the electrical conductor 106. As another example, transverse defects, such as the illustrated crack 128 below the illustrated shelling, also affects the magnetic flux density in the Z-axis direction. In the graph 116, curve 130 represents the magnetic flux density in the Z-axis direction behind the electrical conductor in a rail having the illustrated shelling 124 and the transverse defect 128.

Advantageously, the RFEC effect is not masked by various defects. For example, the shelling 124 does not mask the transverse crack 128. By correlating the measured magnetic flux densities to all types and kinds of defects in the rail, presence of defects can be non-destructively detected. For example, curves and data representing various types of defects may be stored in a look-up-table (LUT) for future use. Accordingly, by correlating a presently measured magnetic flux curve with the data stored in the LUT, for example, the presence of a defect can be determined. As one example, this process of comparison may be performed by a computer program that is stored on one or more tangible media and that directs the processing circuitry 90 (see FIG. 4).

Keeping FIG. 4 in mind, FIG. 6 illustrates an exemplary method for testing material integrity of a rail 74. The exemplary method includes routing an electric current in the flat electrical conductor 76, as represented by block 132. Routing electrical current through the electrical conductor 76 causes certain electromagnetic effects. For example, routing an ac current through the electrical conductor 76 can create RFEC effect in the rail 74. Additionally, routing a dc current through the electrical conductor along with movement of the testing apparatus 72 can also create RFEC effect. The creation of RFEC effect is represented by block 134. As discussed above, resultant magnetic fields from the creation of RFEC effect are affected differently by sections of rail without defects, sections with horizontal defects, and sections with transverse defects under shelling. The magnetic-field sensor 82 detects the magnetic fields (i.e., magnetic flux density) and generates a signal indicative of characteristics of the magnetic fields. This action is represented by block 136. Signals from the magnetic-field sensor 82 may be amplified by an amplifier 84, as indicated by block 138. The amplified magnetic signals can be measured (i.e., quantified) by a gauss-meter 86, as represented by block 140. This data, data from the gauss-meter 86 can be transmitted to a data acquisition module 88, as represented by block 142. The data may be processed by a processing circuitry 90, as represented by block 144. For example, the data may be processed and analyzed to estimate a likelihood of a defect in the rail 74, as represented by block 146.

While only certain features of the invention have been illustrated and described herein, many modifications and changes will occur to those skilled in the art. It is, therefore, to be understood that the appended claims are intended to cover all such modifications and changes as fall within the true spirit of the invention. Indeed, although the present discussion focuses on the testing of rails and railhead, the present technique can be applied to a number of testing environments, such as the testing of plates, bars and support structures, to name but a few environments.

The invention claimed is:

1. A testing apparatus for detecting defects in a test object, comprising:
    an electrical conductor extending in a generally linear direction, wherein the electrical conductor is configured to route current in a generally transverse direction with respect to a longitudinal axis of the test object; and
    a sensing device located a distance from the electrical conductor and configured to detect a magnetic field generated in response to current routed through the electrical conductor.
2. The testing apparatus as recited in claim 1, wherein the electrical conductor is substantially a flat electrical conductor.
3. The testing apparatus as recited in claim 1, comprising a carrier structure configured to direct the electrical conductor in a testing direction along a path of travel generally corresponding with the longitudinal axis of the test object.
4. The testing apparatus as recited in claim 3, wherein the carrier structure is configured to travel along a rail.
5. The testing apparatus as recited in claim 1, wherein the electrical conductor is configured to receive direct current (dc) power.
6. The testing apparatus as recited in claim 1, wherein the electrical conductor is configured to be disposed outboard of an external surface of the test object.
7. The testing apparatus as recited in claim 1, comprising an actuation mechanism configured to position the electrical conductor with respect to the test object.
8. The testing apparatus as recited in claim 1, wherein the electrical conductor is configured to receive alternating current (ac) power.
9. A testing apparatus for detecting defects in a rail of a railroad transportation system, comprising:
    an electrical conductor extending in a generally linear direction and configured to route current in a generally transverse direction with respect to a longitudinal axis of the rail;
    a carrier structure configured to direct the electrical conductor in a testing direction along a path of travel generally parallel to the longitudinal axis of the rail and external to the rail; and
    a magnetic-field sensor located a distance from the electrical conductor and configured to detect a magnetic field generated in response to current routed through the electrical conductor, wherein the magnetic-field sensor travels behind the electrical conductor during movement of the electrical conductor in the testing direction.
10. The testing apparatus as recited in claim 9, wherein the electrical conductor is configured to be disposed adjacent to the rail during testing.
11. The testing apparatus as recited in claim 9, wherein the magnetic-field sensor comprises at least one of a Hall effect sensor and a giant magneto-resistive (GMR) sensor.
12. The testing apparatus as recited in claim 9, comprising a gauss-meter for measuring signals from the magnetic-field sensor.
13. The testing apparatus as recited in claim 9, comprising processing circuitry configured to provide signals indicative of a defect in the rail in response to communications from the magnetic-field sensor.
14. The testing apparatus as recited in claim 13, further comprising a display configured to visually indicate a defect in the rail in response to communications from the processing circuitry.
15. The testing apparatus as recited in claim 9, further comprising wireless communication circuitry configured to transmit and receive information from the magnetic-field sensor in accordance with a wireless protocol.
16. The testing apparatus as recited in claim 9, further comprising network communication circuitry configured to communicate with a remote location via a network.
17. The testing apparatus as recited in claim 9, comprising an alternating current (ac) power source configured to provide ac current to the electrical conductor.
18. The testing apparatus as recited in claim 17, wherein the ac power source comprises a pulse width modulated power source.
19. The testing apparatus as recited in claim 9, comprising a direct current (dc) power source configured to provide dc current to the electrical conductor.
20. A method for detecting defects in a test object, comprising the acts of:
    routing electrical current in a direction generally transverse to a longitudinal axis of a test object via an electrical conductor, such that the electrical current induces eddy currents in the test object; and sensing at least one magnetic field generated in response to the routed electrical current at a distant location from the electrical conductor.

21. The method as recited in claim 20, comprising displacing the electrical conductor in a testing direction generally parallel to the longitudinal axis of the test object along an external surface of the test object.

22. The method as recited in claim 20, comprising the acts of:

measuring the at least one magnetic field using a measuring device; and processing a first set of signals from the measuring device to develop a second set of signals indicative of a defect in the test object.

23. The method as recited in claim 20, comprising sensing the at least one magnetic field that is generated in a direction generally transverse to the longitudinal axis of the test object.

24. The method as recited in claim 20, comprising measuring the magnetic field in a direction generally transverse to the longitudinal axis of the test object.

25. A method for detecting defects in a rail, comprising the acts of:

routing electrical current in a direction generally transverse to a longitudinal axis of the rail via a conductor, such that the electrical current induces eddy currents in the rail;

displacing the conductor in a testing direction generally parallel to the longitudinal axis of the rail; and sensing magnetic field at a location behind the conductor during motion of the conductor in the testing direction.

26. The method as recited in claim 25, comprising routing an alternating current (ac) through the conductor.

27. The method as recited in claim 25, comprising routing a direct current (dc) through the conductor.

28. The method as recited in claim 25, comprising:

amplifying a first set of signals indicative of the magnetic field using an amplifier;

measuring the first set of signals via a measuring device; and processing the first set of signals from the measuring device to develop a second set of signals indicative of a defect in the rail.

29. A method of detecting defects in a test object, comprising:

sensing a magnetic field at a location behind a substantially flat conductor inducing current in the test object in a direction generally transverse to a longitudinal axis of the test object, the magnetic field propagating along an external surface of the test object in a direction generally parallel to the longitudinal axis of the test object; and generating a signal indicative of a defect in the test object based on the sensed magnetic field.

30. The method as recited in claim 29, further comprising correlating the generated signal with a type of defect in the test object.

31. The method as recited in claim 29, comprising sensing a magnetic field at a location behind the substantially flat conductor inducing current in a rail and generating a signal indicative of a defect in the rail.

32. The method as recited in claim 31, comprising correlating the generated signal with a type of defect in the rail.

33. A testing apparatus for detecting defects in a test object, comprising:

means for routing current in a direction generally transverse to a longitudinal axis of the test object;

means for directing the means for routing current in a direction generally parallel to the test object; and means for sensing a magnetic field generated by induced current in the test object at a location behind the means for routing current.

34. A computer program for testing an object, the computer program being disposed on one or more tangible media, comprising:

code for receiving data indicative of a magnetic field generated in response to current routed through a flat electrical conductor in a direction generally transverse to a longitudinal axis of the object, wherein the magnetic field is at a distance from the flat electrical conductor; and code for estimating a defect in the object based on the received data.

* * * * *